United States Patent [19]

Knitter

[11] Patent Number: 4,813,872
[45] Date of Patent: Mar. 21, 1989

[54] FLAVORED SALIVA ABSORBER AND METHOD OF MANUFACTURE

[76] Inventor: Veronica Knitter, 20353 Pkwy., NO. 17, Castro Valley, Calif. 94546

[21] Appl. No.: 12,503

[22] Filed: Feb. 9, 1987

[51] Int. Cl.$^4$ ............................................. A61C 5/14
[52] U.S. Cl. ................................................... 433/136
[58] Field of Search ........................... 433/136; 424/49

[56] References Cited

U.S. PATENT DOCUMENTS

| | | | |
|---|---|---|---|
| 1,438,064 | 12/1922 | Simmons | 433/136 |
| 1,812,655 | 6/1931 | Ladd | 433/136 |
| 2,174,796 | 10/1939 | Luzzi | 433/136 |
| 2,425,945 | 8/1947 | Leach | 128/15 |
| 2,857,908 | 4/1957 | Cornfield | 128/15 |
| 3,120,670 | 6/1960 | Amodeo | 15/167 R |
| 4,071,955 | 2/1978 | Julius | 32/34 |
| 4,192,307 | 5/1978 | Baer | 128/252 |
| 4,293,301 | 6/1979 | Mattsson | 433/136 |
| 4,348,378 | 9/1982 | Kosti | 424/49 |

*Primary Examiner*—John J. Wilson
*Attorney, Agent, or Firm*—Harris Zimmerman; Howard Cohen

[57] ABSTRACT

Absorbers, such as cotton rolls or the like, which are used by dentists to absorb a patient's saliva flow and to space tissue such as the patient's cheek or tongue from the work area are impregnated with a soluble flavoring agent. Gradual release of the flavoring agent during dental procedures creates a pleasurable diversion for the patient which relieves stress and induces better cooperation with the dentist's operations.

4 Claims, 1 Drawing Sheet

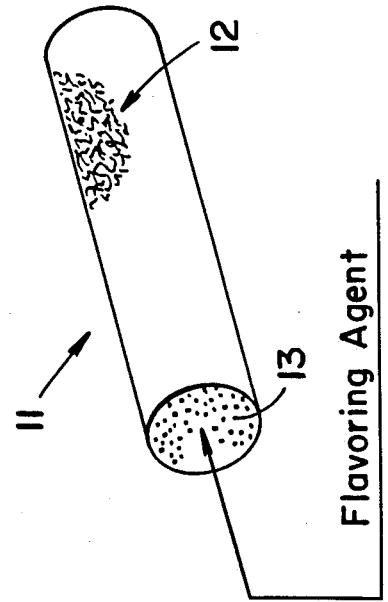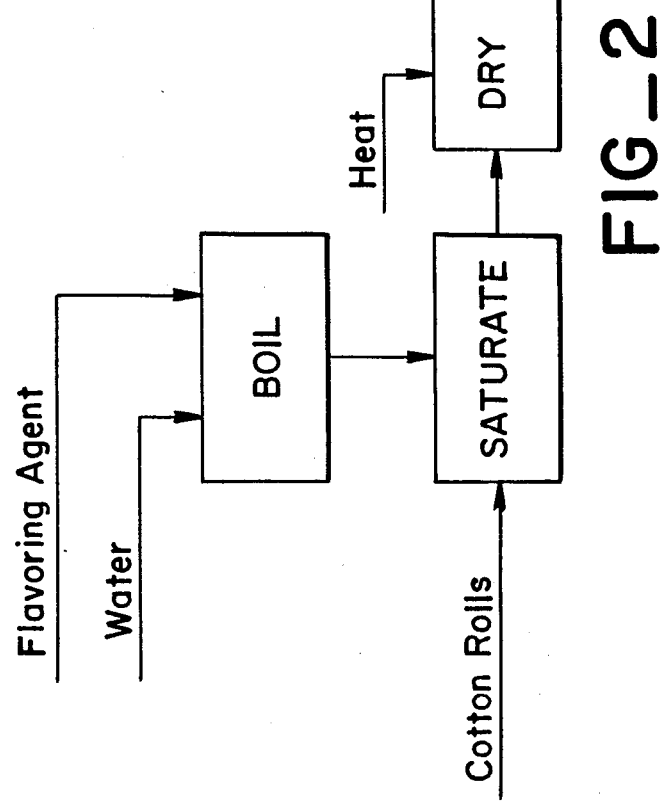

– 4,813,872 –

FLAVORED SALIVA ABSORBER AND METHOD OF MANUFACTURE

TECHNICAL FIELD

This invention relates to dental supplies and more particularly to absorptive rolls, pads, sponges or the like that are used to absorb a patient's saliva flow during dental procedures.

BACKGROUND OF THE INVENTION

Modern anesthetics, equipment and techniques have avoided or greatly reduced the discomfort and pain formerly experienced by dental patients. Because of past associations or for other reasons, many patients continue to be apprehensive during dental operation. This creates problems for the dentist and dental technicians in addition to being stressful to the patient. Patient cooperation is needed for many procedures and is more easily obtained if the patient is in a relaxed, unapprehensive state of mind.

Thus, measures which tend to relax dental patients and to induce pleasurable reactions are highly desirable. In addition to facilitating the work of the dentist and technicians, patients are more likely to seek needed regular dental care if the experiences are remembered as pleasant ones.

Many dental procedures require insertion of a volume of fluid absorbent material into the patient's mouth. The material absorbs saliva flow and may also serve to hold tissue, such as the cheek or tongue, away from the tooth where operations are being performed. Such absorbers are variously referred to as dental rolls, cotton rolls, dental pads or sponges or by other terms depending on the composition and configuration of the absorber. It has not heretofore been recognized that such absorbers can be adapted to serve still another function. In particular, it has not been recognized that absorbers can contribute to relaxation of the patient and be used to induce pleasurable reactions during dental procedures.

The present invention is directed to overcoming one or more of the problems discussed above.

SUMMARY OF THE INVENTION

In one aspect, the present invention provides a saliva absorber having a volume of fluid absorbent material with a configuration suitable for dispostion within the mouth of a dental patient. A flavor releasing substance is disposed in at least a portion of the absorber.

In another aspect of the invention, the flavor releasing substance is a dehydrated water soluble flavoring agent dispersed throughout at least a portion of the volume of fluid absorbent material.

In still another aspect, the invention provides a method for preparing saliva absorbers for use in dental procedures that includes the steps of impregnating at least a portion of a volume of fluid absorbent material with a flavoring agent solution, and subsequently dehydrating the flavoring agent solution within the material.

Absorption of a patient's saliva flow during dental procedures results in a gradual release of the flavoring. The resulting pleasant taste sensation tends to relax patients and induces better cooperation of the patients with the dentist and dental technicians.

BRIEF DESCRIPTION OF THE DRAWING

FIG. 1 is a perspective view of a dental saliva absorber, of the cotton roll form in this example, which embodies the invention.

FIG. 2 is a block diagram illustrating steps in a method for manufacturing flavored saliva absorbers.

DETAILED DESCRIPTION OF THE PREFERRED EMBODIMENTS

Referring initially to FIG. 1 of the drawings, a saliva absorber 11 in accordance with the invention includes a fluid absorbent volume of material 12 having a configuration appropriate for disposition within a dental patient's mouth during dental procedures. The absorber 11 of this particular example is of the cotton roll type in which the absorbent material 12 is a body of highly compressed cotton fibers having a cylindrical configuration suitable for disposition between the gum and cheek tissue or the gum and tongue of a dental patient in the manner known to the art. The invention is equally applicable to saliva absorbers having other shapes for disposition in other parts of the oral cavity and which may be formed of other fluid absorbent materials such as natural or synthetic sponge for example.

At least a portion and preferably all of the fluid absorbent material 12 is impregnated with a flavoring agent 13 which releases a pleasant flavor from the absorber 11 while it is disposed in a dental patient's mouth. In the preferred form, the flavoring agent 13 is a water soluble residue of a dehydrated flavoring solution and is dispersed within the volume of fluid absorbent material 12. A suitable process for forming such a dispersion of dehydrated flavoring agent within the volume of fluid absorbent material will be hereinafter described.

The flavoring agent 13 may be of any the various types which have a pleasant taste such as mint or fruit extracts, chocolate. licorice or others. The flavored saliva absorbers 11 can, if desired be distributed in lots which include a variety of different flavors so that individual dental patients may choose may which particularly suits them.

Referring now to FIG. 2, manufacture of the saliva absorbers 11 may, if desired, proceed in the known conventional manner up to the point where the absorbers have heretofore been considered to be finished product. The saliva absorbers 11, which are cotton rolls in this particular example of the method, are then saturated with a boiled mixture of liquid flavoring and sterile purified water. Mint flavoring No. 19492-3 as manufactured by Flavorence Corp., Los Angeles, CA., is one example of a suitable flavoring agent although many others may also be used as previously pointed out. A mixture of one part of such flavoring to three parts water is suitable for saturating the cotton rolls although the proportions may be varied to emphasize or deemphasize the flavor releasing aspect of the absorbers 11. Dry cotton rolls having a weight of 0.4 grams typically increase in weight to about 3.4 grams upon saturation with such a mixture.

The liquid saturated cotton rolls are then dehydrated until their weight has returned substantially to the original dry weight of 0.4 grams in this particular example. This may be accomplished, for example, by kiln drying at low temperatures for a period of about 60 to 90 minutes. The flavored saliva absorbers 11 may then be packaged for distribution to dental offices. Packaging as well as the above described preceding operations should be accomplished under sterile conditions.

It is preferable in some instances to use a clear liquid flavoring agent, such as that identified above, to avoid discoloration of the saliva absorbers 11. This preserves the typically clean white appearance associated with such products and makes it easier to visually inpect the absorber for possible contamination just prior to use.

The absorbers 11 absorb saliva flow in the conventional manner when placed in a dental patient's mouth. In contrast to the effects of a conventional absorber, this produces a pleasant taste sensation as the flavoring agent is gradually dissolved and released by the accumulating saliva. This tends to divert and relax the patient and to make the dental procedure a generally more enjoyable experience.

While the invention has been disclosed with respect to certain specific embodiments for purpose of example, variations and modifications may be made within the scope of the invention and it is not intended to limit the invention except as defined in the following claims.

I claim:

1. In a saliva absorber having a volume of fluid absorbent material with a configuration suitable for disposition within the mouth of a dental patient, the improvement comprising: a flavor releasing substance disposed in at least a portion of the absorber, said flavor releasing substance being soluble within the mouth to release a predetermined flavor, said fluid absorbent material including a cylindrical roll of fibrous material having said flavor releasing substance distributed therethrough, said fibrous material maintaining said configuration of said volume of material during dissolution of said flavor releasing substance therefrom.

2. The saliva absorber of claim 1 wherein said flavor releasing substance is a dehydrated water soluble flavoring agent dispersed throughout at least a portion of said volume of fluid absorbent material.

3. The saliva absorber of claim 1 wherein said flavor releasing substance is substantially uniformly distributed throughout said volume of fluid absorbent material.

4. The saliva absorber of claim 1 wherein said fluid absorbent material is a fiberous material having internal fibers coated with said flavor releasing substance.

* * * * *